(12) United States Patent
Iida

(10) Patent No.: US 11,141,557 B2
(45) Date of Patent: Oct. 12, 2021

(54) INFORMATION PROCESSING APPARATUS, INFORMATION PROCESSING METHOD, AND STORAGE MEDIUM

(71) Applicant: CANON KABUSHIKI KAISHA, Tokyo (JP)

(72) Inventor: Yoshiko Iida, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 399 days.

(21) Appl. No.: 16/285,682

(22) Filed: Feb. 26, 2019

(65) Prior Publication Data

US 2019/0269881 A1  Sep. 5, 2019

(30) Foreign Application Priority Data

Mar. 1, 2018  (JP) .............................. JP2018-036651

(51) Int. Cl.
| | |
|---|---|
| *G06K 9/00* | (2006.01) |
| *A61M 21/02* | (2006.01) |
| *H04N 21/218* | (2011.01) |
| *G06T 19/00* | (2011.01) |
| *G06T 7/215* | (2017.01) |
| *A61M 21/00* | (2006.01) |

(52) U.S. Cl.
CPC ............ *A61M 21/02* (2013.01); *G06T 7/215* (2017.01); *G06T 19/003* (2013.01); *H04N 21/21805* (2013.01); *A61M 2021/005* (2013.01); *A61M 2205/507* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,574,511 | A * | 11/1996 | Yang ..................... | G03B 17/53 348/586 |
| 7,999,862 | B2 * | 8/2011 | Mack ..................... | H04N 5/272 348/239 |
| 8,788,977 | B2 * | 7/2014 | Bezos .................... | G06F 3/0482 715/863 |
| 9,704,298 | B2 * | 7/2017 | Espeset ................ | G11B 27/031 |

(Continued)

FOREIGN PATENT DOCUMENTS

JP    2013021455 A    1/2013

*Primary Examiner* — Shervin K Nakhjavan

(74) *Attorney, Agent, or Firm* — Carter, DeLuca & Farrell LLP

(57) ABSTRACT

Provided is an information processing apparatus comprising: a first obtaining unit configured to obtain viewpoint information indicating change of a virtual viewpoint corresponding to a virtual viewpoint video generated on the basis of a plurality of images captured from a plurality of directions with a plurality of image capturing apparatuses; a second obtaining unit configured to obtain condition information indicating a condition associated with the amount of change of a background in the virtual viewpoint video; a determination unit configured to determine whether the viewpoint information obtained by the first obtaining unit satisfies the condition indicated by the condition information obtained by the second obtaining unit; and an output unit configured to output information according to the result of the determination by the determination unit.

20 Claims, 14 Drawing Sheets

(56) References Cited

U.S. PATENT DOCUMENTS

| | | | | |
|---|---|---|---|---|
| 2003/0052965 | A1* | 3/2003 | Junkins | G06F 3/011 348/42 |
| 2006/0061567 | A1* | 3/2006 | Ouchi | G06T 13/80 345/419 |
| 2008/0062123 | A1* | 3/2008 | Bell | G06F 3/0425 345/156 |
| 2008/0152192 | A1* | 6/2008 | Zhu | G06K 9/209 382/103 |
| 2009/0315915 | A1* | 12/2009 | Dunn | H04N 5/2621 345/632 |
| 2009/0315978 | A1* | 12/2009 | Wurmlin | G06T 7/20 348/43 |
| 2010/0265171 | A1* | 10/2010 | Pelah | A63F 13/00 345/157 |
| 2011/0242277 | A1* | 10/2011 | Do | G06T 7/90 348/43 |
| 2012/0052947 | A1* | 3/2012 | Yun | A63F 13/833 463/32 |
| 2012/0069131 | A1* | 3/2012 | Abelow | G06Q 10/067 348/14.01 |
| 2014/0037213 | A1* | 2/2014 | Niederberger | G06T 11/00 382/195 |
| 2015/0078621 | A1* | 3/2015 | Choi | G06F 3/011 382/103 |
| 2015/0116357 | A1* | 4/2015 | Moriya | G06F 1/163 345/633 |
| 2016/0088231 | A1* | 3/2016 | Oku | G06T 7/20 348/222.1 |
| 2019/0259189 | A1* | 8/2019 | Tinsman | G06T 11/00 |

* cited by examiner

| CONDITION | 801 CONDITION FOR DETERMINING AMOUNT OF FOREGROUND MOTION | 802 CONDITION FOR DETERMINING AMOUNT OF BACKGROUND MOTION | 803 CAMERA VIEWPOINT-FOREGROUND POSITION DIFFERENCE ANGLE D | 804 CAMERA POSITION | 805 CAMERA ORIENTATION | 806 DIRECTION OF AMOUNT OF BACKGROUND MOTION |
|---|---|---|---|---|---|---|
| 1 | <T1 | >T4 | 0 <= D < D1 | CHANGE | FIXED | HORIZONTAL |
| 2 | <T2 | >T5 | 0 <= D < D1 | FIXED | ROTATE | HORIZONTAL |
| 3 | <T3 | >T6 | 0 <= D < D1 | CHANGE | ROTATE | HORIZONTAL |
| 4 | <T1 | >T7 | 0 <= D < D1 | CHANGE | FIXED | VERTICAL |
| 5 | <T2 | >T8 | 0 <= D < D1 | FIXED | ROTATE | VERTICAL |
| 6 | <T3 | >T9 | 0 <= D < D1 | CHANGE | ROTATE | VERTICAL |
| ... | ... | ... | ... | ... | ... | ... |

FIG.8

INFORMATION PROCESSING APPARATUS, INFORMATION PROCESSING METHOD, AND STORAGE MEDIUM

BACKGROUND OF THE INVENTION

Field of the Invention

The present invention relates to a technique for evaluating visually-induced motion sickness due to a virtual viewpoint video.

Description of the Related Art

There is a virtual viewpoint video technique in which videos captured with a plurality of cameras are used to reproduce a video through a non-existent camera virtually placed in a three-dimensional space (hereinafter, referred to as the virtual camera). In the generation of a virtual viewpoint video, the user can set the virtual camera path (movement of the position of the virtual camera along the time axis) to any path. However, the virtual camera path may cause visually-induced motion sickness depending on how the virtual camera path is set.

From Japanese Patent Laid-Open No. 2013-21455 (hereinafter, referred to as Document 1), a technique has been known in which the degree of discomfort due to video screen movement is estimated to evaluate visually-induced motion sickness. In the technique described in Document 1, a motion vector is detected from each of a plurality of areas divided from the screen to calculate the screen movement, and the degree of discomfort due to the screen movement is estimated.

However, in the technique described in Document 1, the object (foreground) and the background in the video are not separated from each other. For this reason, it is impossible to determine whether screen movement is the result of movement of the object or movement of the background. This lowers the accuracy of the visually-induced motion sickness evaluation.

SUMMARY OF THE INVENTION

An information processing apparatus according to an aspect of the present invention comprises: a first obtaining unit configured to obtain viewpoint information indicating change of a virtual viewpoint corresponding to a virtual viewpoint video generated on a basis of a plurality of images captured from a plurality of directions with a plurality of image capturing apparatuses; a second obtaining unit configured to obtain condition information indicating a condition associated with an amount of change of a background in the virtual viewpoint video; a determination unit configured to determine whether the viewpoint information obtained by the first obtaining unit satisfies the condition indicated by the condition information obtained by the second obtaining unit; and an output unit configured to output information according to a result of the determination by the determination unit.

Further features of the present invention will become apparent from the following description of exemplary embodiments with reference to the attached drawings.

BRIEF DESCRIPTION OF THE DRAWINGS

FIG. 8 is a diagram listing evaluation conditions for evaluating visually-induced motion sickness;

DESCRIPTION OF THE EMBODIMENTS

Embodiments of the present invention will be described below with reference to the drawings. Note that the following embodiments do not limit the present invention, and not all the combinations of the features described in these embodiments are necessarily essential for a solution provided by the present invention. Meanwhile, the description will be given with the same reference sign given to identical components.

Embodiment 1

<Configuration of Image Processing Apparatus>

Figure 1:
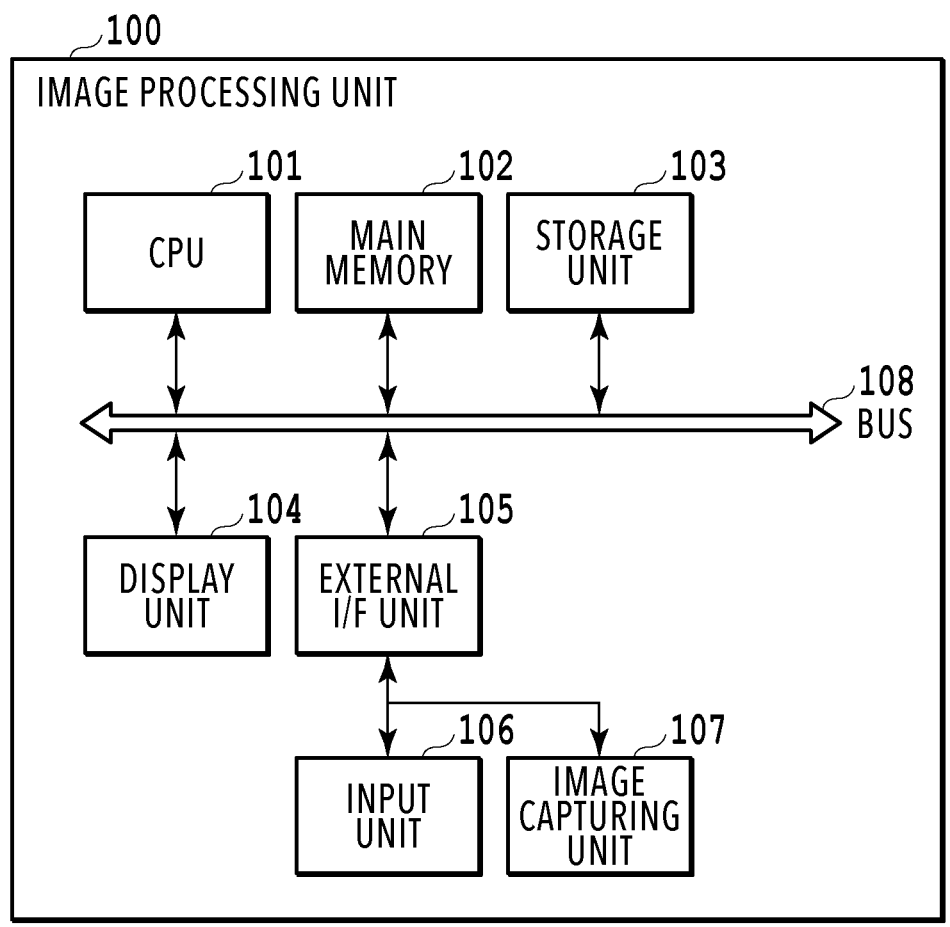
FIG. 1 is a diagram illustrating an example of the configuration of an image processing apparatus.

FIG. 1 is a diagram illustrating an example of the configuration of an image processing apparatus in embodiment 1. An image processing apparatus 100 illustrated in FIG. 1 includes a CPU 101, a main memory 102, a storage unit 103, a display unit 104, and an external I/F unit 105, which are connected to each other through a bus 108. The CPU 101 is an arithmetic processing device that controls the whole image processing apparatus 100, and performs various processes by executing various programs stored in the storage unit 103 or the like. The main memory 102 temporarily stores pieces of data, parameters, and so on to be used in the various processes and also provides a work area to the CPU 101. The storage unit 103 is a large-capacity storage apparatus storing various programs and various pieces of data necessary for displaying graphical user interfaces (GUIs). As the storage unit 103, a non-volatile memory such as a hard disk drive or a silicon disk is used, for example. The display unit 104 is formed of a liquid crystal panel or the like, and displays GUIs for setting a virtual camera path during the generation of a virtual viewpoint video and so on.

The external I/F unit 105 allows an input unit 106 such as a keyboard, a mouse, an electronic pen, a touchscreen, etc. and image capturing units 107 such as cameras to be connected to the bus 108, and transmits and receives video data and control signal data.

Note that the image processing apparatus 100 illustrated in FIG. 1 is a mere example, and the present invention is not limited to this. For example, the image processing apparatus 100 may not include the display unit 104 and the image capturing unit 107. In one example, the image processing apparatus 100 may include a display control unit (not illustrated), with which the image processing apparatus 100 may control display by a display apparatus (not illustrated) equivalent to the display unit 104. Also, the image processing apparatus 100 may receive and transmit video data and control signal data from and to image capture apparatuses (not illustrated) equivalent to the image capturing units 107.

Figure 2:
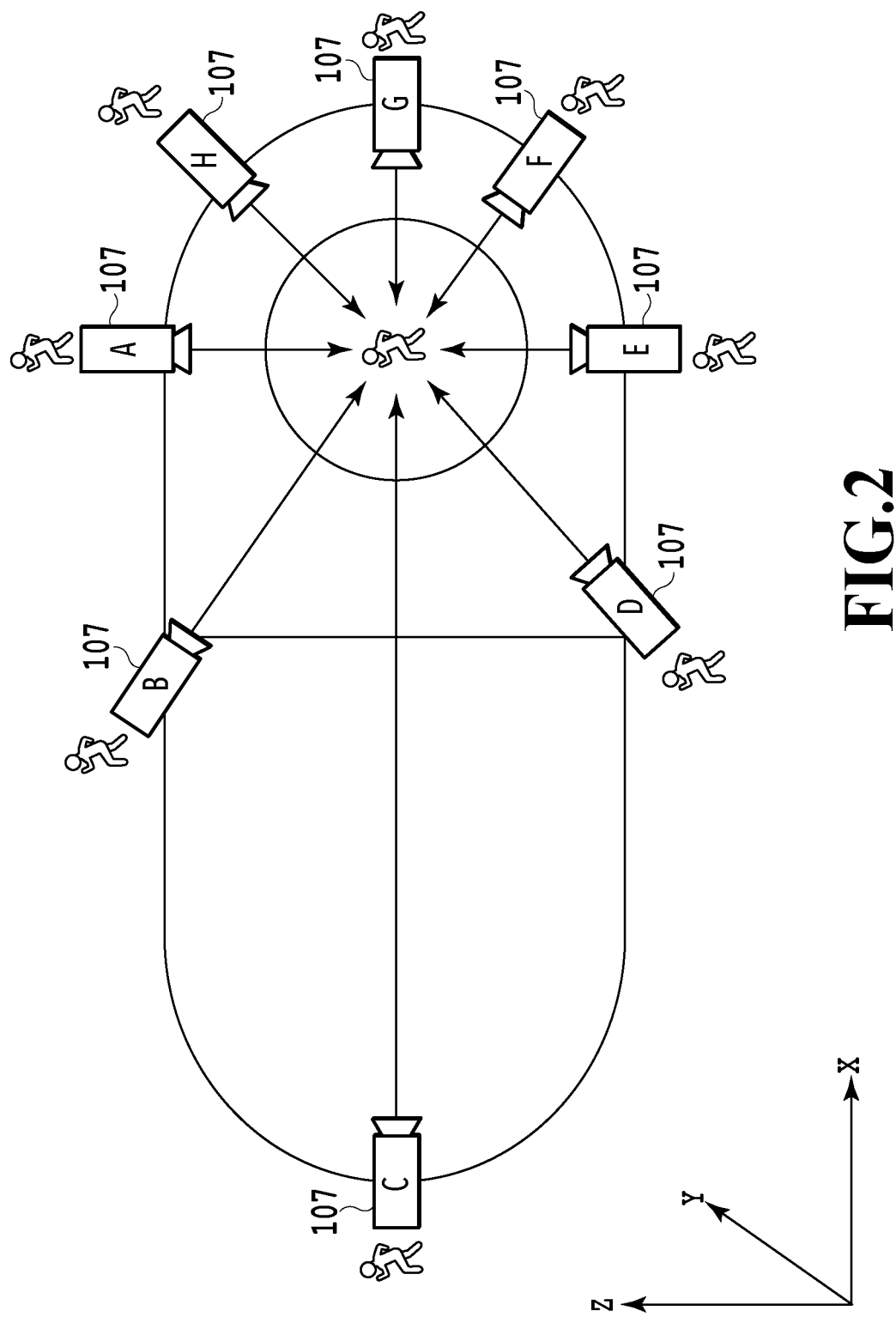
FIG. 2 is a diagram illustrating an example of camera arrangement.

FIG. 2 is a diagram illustrating an example of the image capturing units 107 in this embodiment. FIG. 2 illustrates an example in which eight image capturing units 107 are placed in a sports venue for playing soccer and so on. Camera viewpoints A to H are directed toward a gazing point located at the center of a circle. The image capturing units 107 are arranged such that the angle formed between the camera viewpoints of each pair of adjacent image capturing units is equal.

Figure 3:
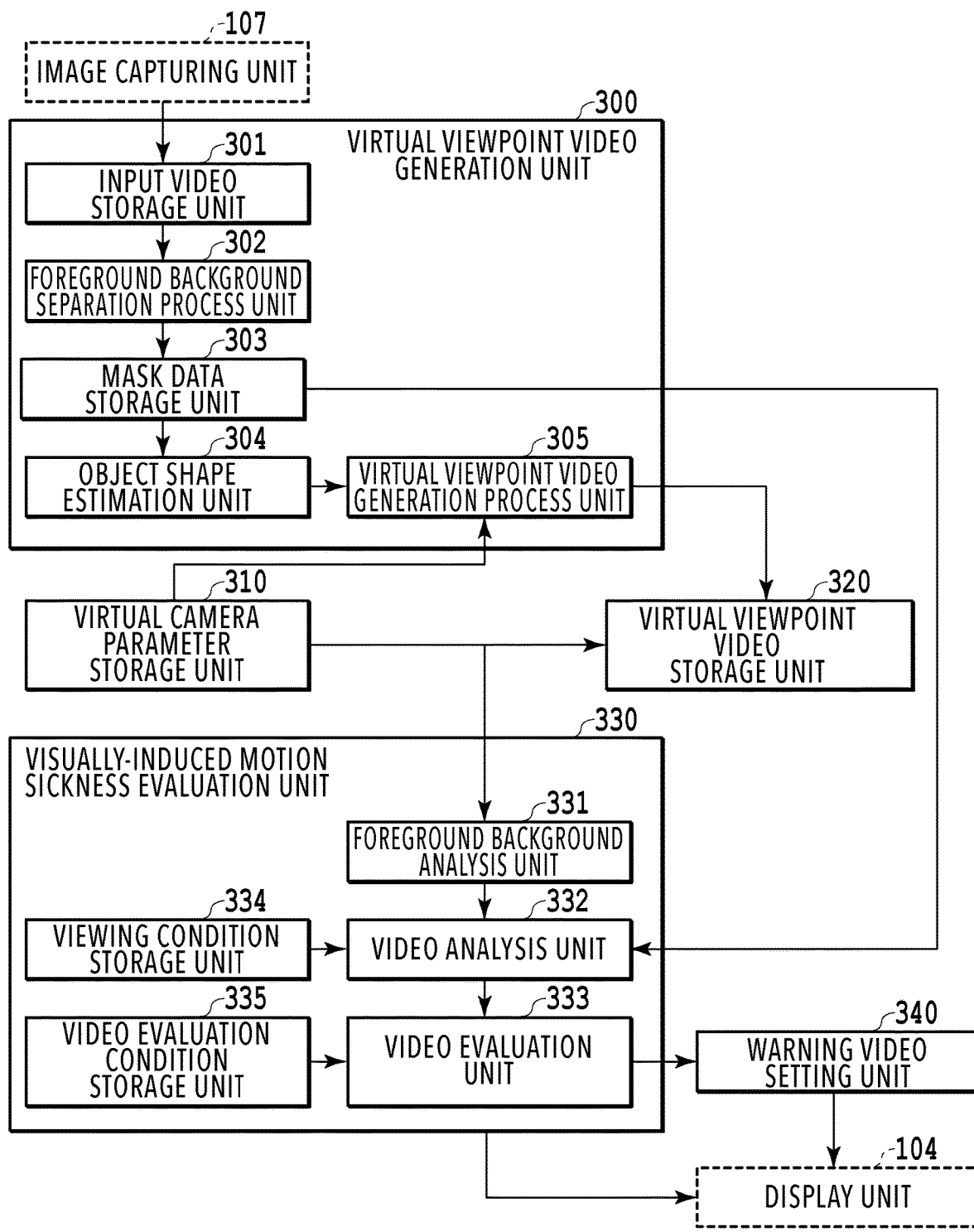
FIG. 3 is a diagram illustrating an example of the logical configuration of the image processing apparatus.

FIG. 3 is a diagram illustrating an example of the logical configuration of the image processing apparatus 100. The image processing apparatus 100 includes a virtual viewpoint video generation unit 300, a virtual camera parameter storage unit 310, a virtual viewpoint video storage unit 320, a visually-induced motion sickness evaluation unit 330, and a warning video setting unit 340.

The virtual viewpoint video generation unit 300 generates virtual viewpoint video data following a virtual camera path (a path along which the virtual viewpoint is caused to move) designated by the user by using a plurality of videos (frame images) corresponding to a plurality of viewpoints captured by image capturing units 107. The generated virtual viewpoint video data is stored in the virtual viewpoint video storage unit 320. Also, virtual camera parameters representing the virtual camera path used in the generation of the virtual viewpoint video data is stored in the virtual camera parameter storage unit 310. The virtual camera parameters stored in the virtual camera parameter storage unit 310 indicate the positions and directions of the virtual viewpoint at a plurality of time points (frames) included in the playback period of the virtual viewpoint video. In short, the virtual camera parameters stored in the virtual camera parameter storage unit 310 are viewpoint information indicating change of the virtual viewpoint during that playback period. In the following, for simple description, virtual viewpoint video data to be generated and stored will be simply referred to as a virtual viewpoint video.

The visually-induced motion sickness evaluation unit 330 uses the virtual viewpoint video stored in the virtual viewpoint video storage unit 320 and the virtual camera path used in the generation of that virtual viewpoint video to evaluate visually-induced motion sickness due to the virtual viewpoint video. The visually-induced motion sickness evaluation unit 330 identifies a video scene on the basis of the virtual camera path and the virtual viewpoint video, and then evaluates the visually-induced motion sickness by using an evaluation condition corresponding to the specified video image.

There are videos that are similar to each other but one is likely to cause visually-induced motion sickness while the other is unlikely to cause visually-induced motion sickness. When it comes to a virtual viewpoint video, the relation between the object and the pattern of movement of the virtual camera may change whether the virtual viewpoint video is likely to cause motion sickness. For example, a virtual viewpoint video generated as a scene in which the object is still and the virtual camera moves around it and a virtual viewpoint video generated as a scene in which the camera follows and moves in parallel with the object are similar. However, the former is likely to cause visually-induced motion sickness while the latter is unlikely to cause visually-induced motion sickness. The visually-induced motion sickness evaluation unit 330 identifies the video scene and performs a visually-induced motion sickness evaluation by using an evaluation condition corresponding to the identified video scene. In this way, an accurate visually-induced motion sickness evaluation can be performed. Specifically, the visually-induced motion sickness evaluation unit 330 performs a process using such an evaluation condition that a scene that is likely to cause visually-induced motion sickness is likely to be evaluated as a video that is likely to cause motion sickness. Details will be described later.

The warning video setting unit 340 sets a warning video to be displayed on the display unit 104 depending on the result of the visually-induced motion sickness evaluation by the visually-induced motion sickness evaluation unit 330. The set warning video is displayed on the display unit 104.

The virtual viewpoint video generation unit 300 includes an input video storage unit 301, a foreground background separation process unit 302, a mask data storage unit 303, an object shape estimation unit 304, and a virtual viewpoint video generation process unit 305. The visually-induced motion sickness evaluation unit 330 includes a foreground background analysis unit 331, a video analysis unit 332, a video evaluation unit 333, a viewing condition storage unit 334, and a video evaluation condition storage unit 335.

In the logical configuration in FIG. 3, the storage units, which store various pieces of data and videos, are implemented in the main memory 102 or the storage unit 103, for example. As for the other units of the logical configuration, the CPU 101 executes programs stored in the storage unit 103 or the like to function as those units in FIG. 3. Note that in the example of FIG. 3, the image processing apparatus 100 may be configured as an apparatus that implements the visually-induced motion sickness evaluation unit 330, and the other units in the configuration may be implemented with other apparatuses, for example. In short, the logical configuration illustrated in FIG. 3 may be a configuration implemented with a plurality of image processing apparatuses such that the processing is distributed.

<Virtual Viewpoint Video Generation Process>

Figure 4:
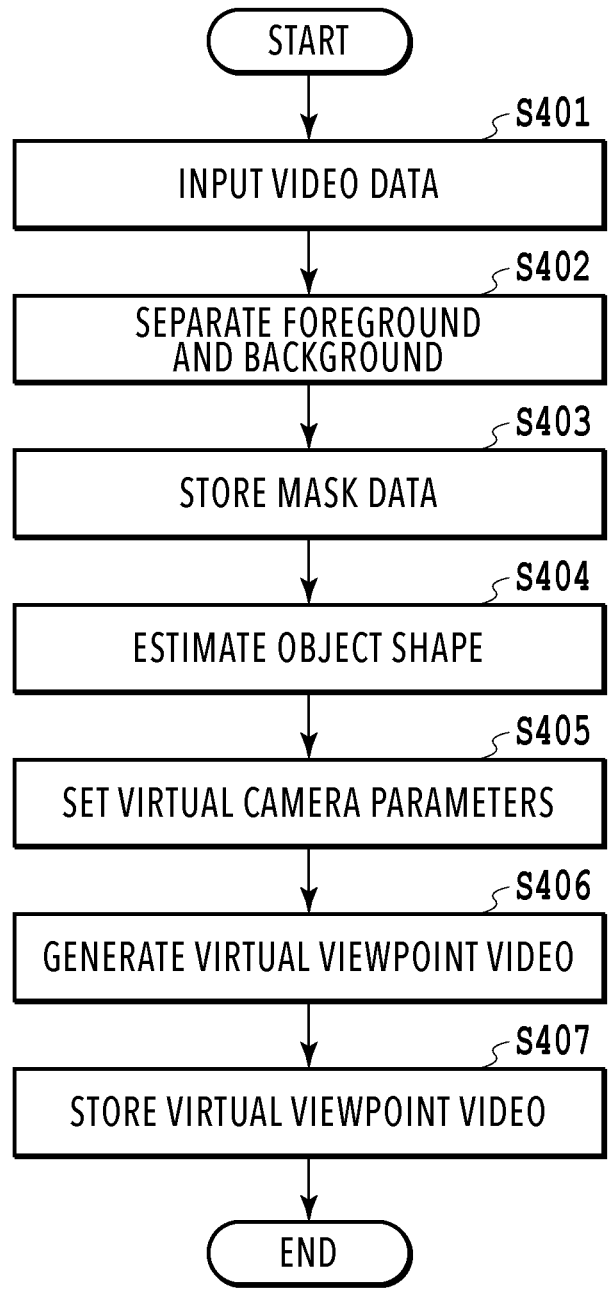
FIG. 4 is a flowchart describing the flow of a process by the image processing apparatus.

FIG. 4 is a diagram illustrating an exemplary flowchart of a process of generating a virtual viewpoint video performed by the virtual viewpoint video generation unit 300. The process illustrated in FIG. 4 is implemented as the CPU 101 reads a predetermined program out of the storage unit 103, decompresses the read program onto the main memory 102, and executes this decompressed program. Alternatively, the functions of some or all of the steps in FIG. 4 may be implemented with hardware such as an ASIC or an electronic circuit. Meanwhile, the symbol "S" in the description of each process means a step in the flowchart (the same applies throughout this specification).

In S401, the image capturing units 107 corresponding to the plurality of viewpoints in FIG. 2 (camera viewpoints A to H) capture images from the respective viewpoints in synchronization with each other and store the pieces of video data from the camera viewpoints (pieces of frame image data) in the input video storage unit 301.

In S402, the foreground background separation process unit 302 executes a foreground background separation process on each of the frame images from the camera viewpoints by extracting, from the frame image, a pixel area corresponding to a predetermined object as the foreground and the remaining pixel area as the background. Further, the foreground background separation process unit 302 generates mask data formed of the pixel area extracted as the foreground. The mask data is an image in which the background is masked and the foreground is extracted.

There are known foreground background separation techniques such as a process involving comparing frame images with each other and extracting an object, which is a foreground, on the basis of the amount of displacement of each pixel. For this step, any method may be employed as long as it is a process that separates the foreground and the background from the image.

In S403, the foreground background separation process unit 302 stores the mask data generated in S402 in the mask data storage unit 303.

In S404, the object shape estimation unit 304 executes a process of estimating the three-dimensional shape of the object by using the frame image from each camera viewpoint, parameters indicating the position, orientation, and so on of each image capturing unit 107, and the mask data. As the estimation method, a publicly known method may be used such as a visual hull method, which uses information on an object's silhouette, or a multi-view stereo method, which uses triangulation. The object shape estimation unit 304 also estimates the coordinate positions of the object within the virtual space for generating the virtual viewpoint video.

In S405, the virtual viewpoint video generation unit 300 sets the virtual camera parameters in the virtual viewpoint video and stores them in the virtual camera parameter storage unit 310. The virtual camera parameters include the camera coordinate values, the camera orientation, the focal length, and so on in each of the video frames (frame images) along the time axis inside the virtual space for generating the virtual viewpoint video. Specifically, with the virtual camera parameters, it is possible to identify at least one of the changes in speed, acceleration, deceleration, direction, position, and orientation of the virtual camera. The virtual camera parameters are input by the user through the input unit 106, for example.

In S406, the virtual viewpoint video generation process unit 305 generates a virtual viewpoint video in accordance with the set virtual camera parameters. The virtual viewpoint video is generated by applying a computer graphics technique to a video in which the estimated object shape at its estimated position is viewed from the set virtual camera.

In S407, the virtual viewpoint video generation process unit 305 stores the generated virtual viewpoint video in the virtual viewpoint video storage unit 320. The virtual viewpoint video generation unit 300 generates a virtual viewpoint video in this manner. Note that the virtual viewpoint video generation process may be performed by an apparatus other than the image processing apparatus 100, which performs a visually-induced motion sickness evaluation. The above is the basic procedure to the point where a virtual viewpoint video is generated.

<Overview of Visually-Induced Motion Sickness Evaluation Process>

Figure 5:
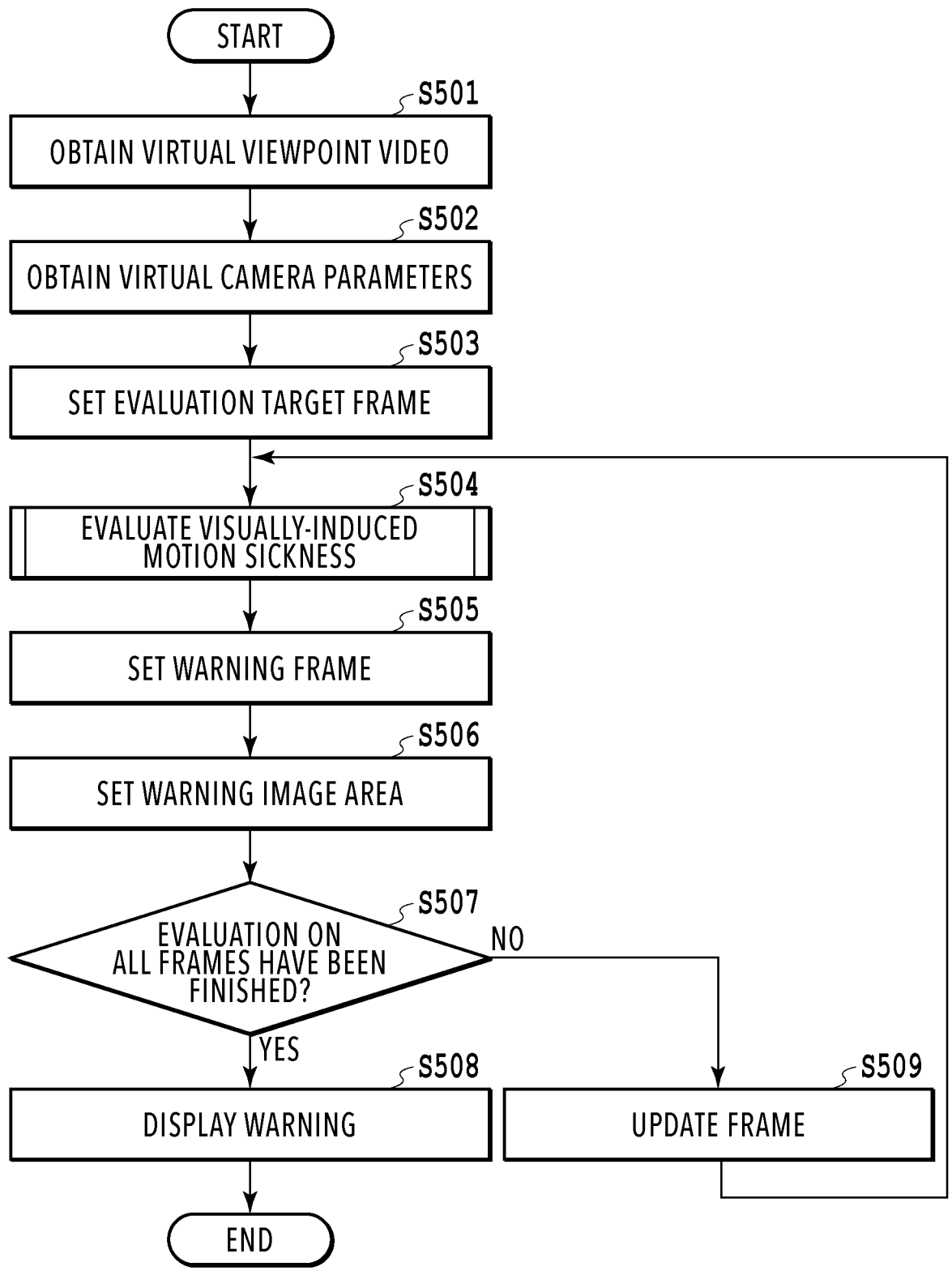
FIG. 5 is a flowchart describing the flow of a process by the image processing apparatus.

FIG. 5 is a diagram illustrating an exemplary flowchart of a visually-induced motion sickness evaluation process performed by the visually-induced motion sickness evaluation unit 330. FIG. 5 is a flowchart describing the entire procedure to a point where the visually-induced motion sickness evaluation unit 330 evaluates visually-induced motion sickness due to an obtained virtual viewpoint video and displays a warning for any frame region that is highly likely to cause visually-induced motion sickness.

In S501, the visually-induced motion sickness evaluation unit 330 obtains a virtual viewpoint video stored in the virtual viewpoint video storage unit 320. For example, a plurality of virtual viewpoint videos can be stored in the virtual viewpoint video storage unit 320. The visually-induced motion sickness evaluation unit 330 obtains a virtual viewpoint video stored as an evaluation target video from among the virtual viewpoint videos stored in the virtual viewpoint video storage unit 320.

In S502, the visually-induced motion sickness evaluation unit 330 obtains the virtual camera parameters used for the evaluation target virtual viewpoint video, which are stored in the virtual camera parameter storage unit 310.

In S503, the visually-induced motion sickness evaluation unit 330 sets a frame image to be evaluated (hereinafter, also referred to as the evaluation target frame) in the virtual viewpoint video obtained in S501. For example, the visually-induced motion sickness evaluation unit 330 may set an evaluation target frame on the basis of a designation from the user or set an evaluation target frame at preset time intervals. The visually-induced motion sickness evaluation unit 330 may set an evaluation target frame in a case where any of predetermined scenes is present.

In S504, the visually-induced motion sickness evaluation unit 330 refers to a visually-induced motion sickness evaluation condition for the evaluation target frame set in S503. Then, the visually-induced motion sickness evaluation unit 330 determines the likelihood of occurrence of visually-induced motion sickness on the basis of the visually-induced motion sickness evaluation condition. Details will be described later.

In S505, the warning video setting unit 340 sets a warning flag for the evaluation target frame set in S503 if the visually-induced motion sickness evaluation unit 330 determines that the evaluation target frame is a frame image that is highly likely to cause visually-induced motion sickness. Namely, the warning video setting unit 340 sets a warning frame for the evaluation target frame set in S503.

In S506, from the frame image determined to be highly likely to cause visually-induced motion sickness, the warning video setting unit 340 extracts an image area that can be a cause of the visually-induced motion sickness, and sets the image area as a warning display area.

In S507, the visually-induced motion sickness evaluation unit 330 determines whether all frame images in the evaluation target virtual viewpoint video have been evaluated. If there is any frame image yet to be evaluated, the visually-induced motion sickness evaluation unit 330 updates the evaluation target frame in S509, and the processes in and after S504 are repeated.

If the evaluation on all frame images has been completed, then in S508, the visually-induced motion sickness evaluation unit 330 displays the result of the visually-induced motion sickness evaluation on the virtual viewpoint video on the display unit 104, and the process in this flowchart is terminated. In S508, a warning is displayed on any frame evaluated to cause visually-induced motion sickness. Note, however, that the result of the visually-induced motion sickness evaluation on each single frame may be displayed thereon in the form of a numerical value or another form of information. Also, for frames evaluated not to cause visually-induced motion sickness, information indicating that evaluation result may be displayed thereon.

The process described in FIG. 5 represents an example in which a visually-induced motion sickness evaluation is performed on a virtual viewpoint video generated by the virtual viewpoint video generation unit 300 in the image processing apparatus 100. Note, however, that the present invention is not limited to this. The image processing apparatus 100 may receive a virtual viewpoint video generated by another apparatus and evaluate visually-induced motion sickness due to that virtual viewpoint video. Alternatively, the image processing apparatus 100 may read out a virtual viewpoint video stored in a storage medium not illustrated and evaluate visually-induced motion sickness due to that virtual viewpoint video.

<Details of Visually-Induced Motion Sickness Evaluation>

Figure 6:
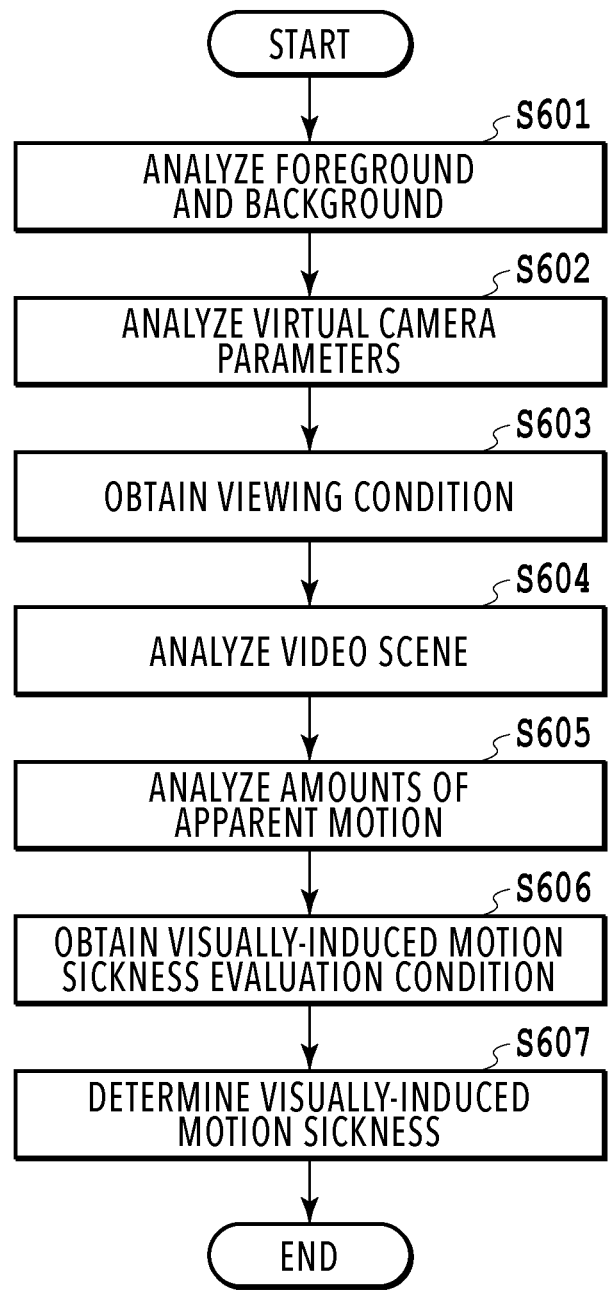
FIG. 6 is a flowchart describing the flow of a process by the image processing apparatus.

FIG. 6 is a flowchart describing details of the visually-induced motion sickness evaluation process listed in S504 in FIG. 5. Details of the visually-induced motion sickness evaluation will be described below with reference to the configuration diagram of FIG. 3 and the flowchart of FIG. 6.

In S601, the foreground background analysis unit 331 performs an analysis process on the foreground and background image areas in the evaluation target frame (virtual viewpoint video) and separates the evaluation target frame into the foreground and the background. For example, the foreground background analysis unit 331 may separate the evaluation target frame into the foreground and the background on the basis of the pixel-by-pixel differences from preceding and subsequent frame images. Alternatively, the foreground background analysis unit 331 may use the mask data of the foreground stored in the mask data storage unit 303 to generate a virtual viewpoint video of the foreground mask data via a process equivalent to the process performed by the virtual viewpoint video generation unit 300, and use this mask data to separate the virtual viewpoint video into foreground and background image areas. Still alternatively, in the generation of the virtual viewpoint video by the virtual viewpoint video generation unit 300, its foreground area may be converted into mask data and stored, and the foreground background analysis unit 331 may use this stored mask data to separate the evaluation target frame into foreground and background image areas.

The foreground background analysis unit 331 detects the amounts of displacement of the separated foreground and background image areas between frames. For example, the foreground background analysis unit 331 detects the amounts of displacement of the foreground and background image areas between frames by using a commonly known motion vector detection process. These amounts of displacement are the amounts of motion in the video size (pixel) (the amounts of motion in terms of pixels). Further, the foreground background analysis unit 331 also obtains information on the position of the separated foreground in the frame image.

Meanwhile, the process in S601 may be executed for all evaluation target frames when the visually-induced motion sickness evaluation unit 330 obtains the evaluation target virtual viewpoint video. In this case, the process in S601 may be changed to a process of obtaining the data that has already been analyzed and stored. In short, the foreground background separation process may not be performed individually on each evaluation target frame, but the separation process may be performed collectively on the evaluation target virtual viewpoint video. Alternatively, only the separation process may be performed in advance, and S601 may simply be the process of detecting the amounts of displacement of the foreground and background image areas between frames.

In S602, the video analysis unit 332 performs a virtual camera parameter analysis process. The video analysis unit 332 obtains the virtual camera parameters used for the evaluation target frame image in the virtual viewpoint video, and obtains the amount of change in virtual camera coordinates and the amount of change in camera orientation.

In S603, the video analysis unit 332 obtains a viewing condition stored in the viewing condition storage unit 334. The viewing condition is the condition under which the virtual viewpoint video is to be viewed by the user. The viewing condition is set by the user. The viewing condition includes at least a display condition and an environmental condition. The display condition is, for example, the size in which the virtual viewpoint video is to be displayed. The environmental condition is, for example, information on the distance between the user who is to view the virtual viewpoint video and the displayed video. Other viewing conditions may be included such as the display device's type, brightness, and dynamic range, and the conditions of surroundings in the viewing environment (such as lighting). The viewing condition may also include profile information on user characteristics such as the age and sex of the user who is to view the virtual viewpoint video and the user's susceptibility to motion sickness, and so on. Visually-induced motion sickness can be dependent on the actual viewing environment in which the user views the virtual viewpoint video. For example, if the same video is viewed on a large screen in a theater or the like and on a tablet terminal, a home television set, or the like, motion sickness may be likely to occur in the former case while motion sickness may be unlikely to occur in the latter case. For this reason, the visually-induced motion sickness evaluation is performed with the viewing condition taken into consideration.

In S604, the video analysis unit 332 analyzes the video scene of the evaluation target frame. The video analysis unit 332 determines the foreground to be defined as the main object in the evaluation target frame. Then, the video analysis unit 332 obtains the amounts of change of the foreground defined as the main object and the virtual camera path.

In S605, the video analysis unit 332 determines the amounts of apparent motion of the foreground and the background in the video to be viewed by the viewer by using the viewing condition obtained in S603. For example, the video analysis unit 332 determines the amounts of apparent motion in the video by referring to the amounts of displacement of the foreground and the background obtained by the analysis process in S601, the video display size in which the virtual viewpoint video is to be viewed by the user, and the distance between the user and the displayed video. Motion direction vectors and angular speeds in the viewer's view are determined as the amounts of motion. Note that the background area may be divided, and the amount of apparent motion in each divided area may be determined. A speed value other than angular speed may be used instead.

In S606, the video evaluation unit 333 obtains a visually-induced motion sickness evaluation condition that matches the result of the analysis in S604 and the amounts of apparent motion obtained in S605 from among visually-induced motion sickness evaluation conditions stored in the video evaluation condition storage unit 335. Thus, in this embodiment, the evaluation condition (evaluation parameters) for evaluating visually-induced motion sickness is varied in accordance with the video scene. This will be described below with reference to specific examples.

Figure 7A:
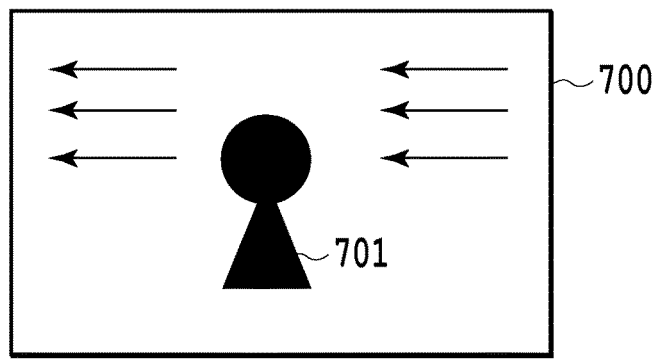
FIGS. 7A to 7D are diagrams illustrating relations between an object and virtual camera paths.

FIGS. 7A to 7D are diagrams explaining video scenes. The relations between a main object, which is a foreground, and virtual camera paths in virtual viewpoint videos will be described with reference to FIGS. 7A to 7D. FIG. 7A is a diagram schematically illustrating a motion vector in a given frame image 700 in a virtual viewpoint video. In the video scene of FIG. 7A, an object 701 appears to be still in the center of the virtual viewpoint video. The background, on the other hand, appears to be moving from right to left.

Figure 7B:
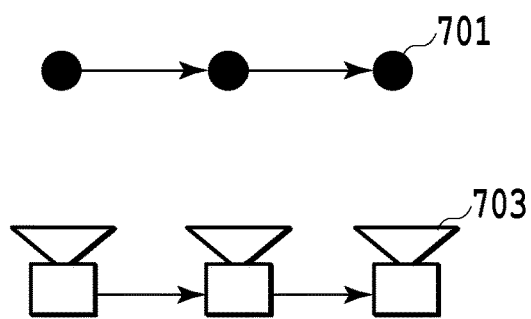
Figure 7C:
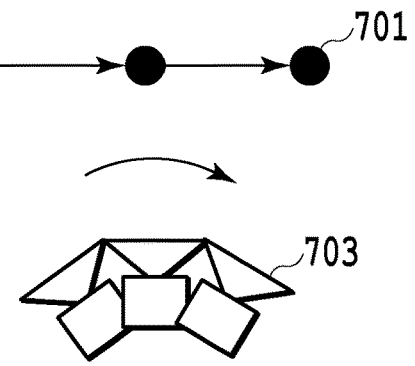
Figure 7D:
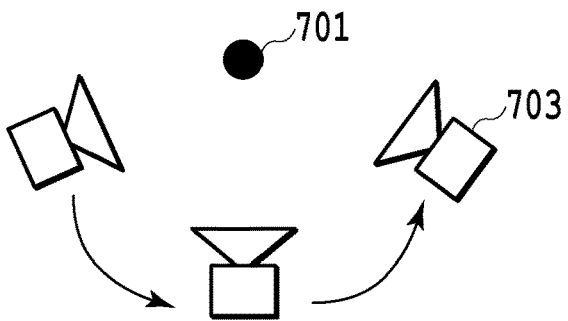

FIGS. 7B to 7D are diagrams each illustrating the relation between changes in the position of the object 701 in the three-dimensional virtual space in a virtual viewpoint video and changes in the position and orientation of a virtual camera 703.

FIG. 7B represents a virtual camera path along which the virtual camera 703 follows the object 701 that is moving, while maintaining the distance therebetween within a certain range without changing the orientation.

FIG. 7C represents a virtual camera path along which the virtual camera 703 does not greatly change its position with respect to the object 701 that is moving, but changes its orientation to follow the motion of the object.

FIG. 7D represents a virtual camera path along which the virtual camera 703 moves around the object 701 that is hardly changing in position, while maintaining the distance therebetween within a certain range.

The relations between the object 701 and the virtual camera paths in FIGS. 7B to 7D are different from each other. However, in each of the virtual viewpoint videos generated with these camera paths, the motions of the object and the background are similar to those illustrated FIG. 7A. In other words, even in a case where video scenes contain substantially the same apparent motions as those in the frame image 700, the motions of the object and the background and the virtual camera path may be different. Moreover, the degree of visually-induced motion sickness which video viewers experience (likelihood of visually-induced motion sickness) from the apparent motions in a video varies. Specifically, as for the degree of visually-induced motion sickness which video viewers experience from the apparent motions in the virtual viewpoint video illustrated in FIG. 7A, is highest with FIG. 7D, so that FIG. 7D is most likely to cause motion sickness. FIG. 7C and FIG. 7B cause lower degrees of visually-induced motion sickness in this order and are therefore videos less likely to cause motion sickness in this order.

As described above, even if videos contain the same amounts of motion of the object and the background, the degree of visually-induced motion sickness caused by those amounts of motion may vary depending on the relation between the object and the virtual camera path. Thus, the evaluation condition for evaluating whether the video causes visually-induced motion sickness is preferably changed in accordance with the video scene. Specifically, the evaluation condition for evaluating visually-induced motion sickness is preferably changed in accordance with the motions of the object and the background and the virtual camera path. The motions of the object and the background can include at least one of changes in speed, acceleration, deceleration, direction, and position of the object and the background.

In this embodiment, the evaluation condition is determined on the basis of the video scene of the evaluation target frame. Specifically, the evaluation condition for evaluating visually-induced motion sickness is determined in accordance with the motions of the object and the background in the evaluation target frame and the virtual camera path. Then, a visually-induced motion sickness evaluation is performed on the basis of the determined evaluation condition.

FIG. 8 is a diagram explaining evaluation conditions for evaluating visually-induced motion sickness. In FIG. 8, evaluation conditions with different degrees of visually-induced motion sickness corresponding to amounts of displacement of the foreground defined as the main object and types of virtual camera movement track are defined. Evaluation conditions 800 are stored in the video evaluation condition storage unit 335 in advance.

The video analysis unit 332 analyzes the video scene and determines the foreground to be defined as the main object from among the plurality of foregrounds present in the evaluation target frame by referring to a condition 803. In this embodiment, a condition for determining, as the main object, a foreground present within a predetermined angular range centered on the virtual camera viewpoint is set.

Under conditions 804 to 806, evaluation conditions are set which are combinations of change in the position of the virtual camera, the orientation of the virtual camera, and the direction of apparent motion of the background under the viewing condition. Note that the direction of the amount of background motion takes the viewing condition obtained in S603 into consideration since there can be a change in direction (such as viewing the video sideways) depending on the viewing condition. Under a condition 801, conditions on the amount of apparent motion of the main object in the virtual viewpoint video are stored. By combining the above conditions, an evaluation condition corresponding to the video scene is determined.

Here, the evaluation conditions in FIG. 8 cover evaluation conditions for the video scenes of the virtual viewpoint videos illustrated in FIGS. 7B to 7D. Specifically, the evaluation conditions in FIG. 8 cover evaluation conditions for scenes in virtual viewpoint videos in which, in the user's view, the change in position of the main object on the screen is small and the change of the background on the screen is large (the background moves). The condition 801 covers conditions on the amount of change of the main object area (foreground) (conditions each defining whether the amount of change of the foreground is smaller than a predetermined threshold value). A condition 802 cover conditions on the amount of change of the background (conditions each defining whether the amount of change of the background is smaller than a predetermined threshold value). In this case, the visually-induced motion sickness evaluation is performed on the basis of the amounts of apparent motion of the background listed under the condition 802. Specifically, in the case of using an evaluation condition listed in FIG. 8, the video scene is determined by the condition 801 and the conditions 804 to 806, and an evaluation condition corresponding to that video scene is determined by referring to the condition 802.

In the example presented above, the video scene is determined on the basis of the amount of motion of the foreground and the combination of the change in position of the virtual camera and the orientation of the virtual camera, and the amount of motion of the background corresponding to that video scene is used as the evaluation condition. Note, however, that the present invention is not limited to this. The video scene may be determined on the basis of the amount of motion of the background and the combination of the change in position of the virtual camera and the direction of the virtual camera, and the amount of motion of the foreground corresponding to that video scene may be used as the evaluation condition. Alternatively, the video scene may be determined on the basis of the amounts of motion of the foreground and the background and the combination of the change in position of the virtual camera and the direction of the virtual camera, and the amounts of motion of the foreground and the background corresponding to that video scene may be used as the evaluation condition.

Also, the condition for distinguishing between scenes with different degrees of visually-induced motion sickness, and the evaluation condition for evaluating visually-induced motion sickness may be a condition for any of changes in speed, acceleration, deceleration, direction, and position of the foreground or the background, and a condition for any of changes in speed, acceleration, deceleration, direction, position, and orientation of the virtual camera.

Also, in the example described, the video display size in which the virtual viewpoint video is to be viewed by the user, and the distance between the user and the displayed video are referred to as the viewing condition. However, other viewing conditions may be taken into consideration. These other viewing conditions may include the display device's type, brightness, and dynamic range, and the conditions of surroundings in the viewing environment (such as lighting). The viewing condition may also include profile information on user characteristics such as the age and sex of the user who is to view the virtual viewpoint video and the user's susceptibility to motion sickness, and so on. Different visually-induced motion sickness evaluation conditions corresponding to these viewing condition elements may be stored in the video evaluation condition storage unit 335, and an appropriate evaluation condition may be selected in accordance with the viewing condition.

Referring back to FIG. 6, the description will be continued. In S607, on the basis of the visually-induced motion sickness evaluation condition obtained in S606, the video evaluation unit 333 evaluates whether the condition is satisfied (whether the video causes visually-induced motion sickness). With the video scene examples in FIG. 7B to 7D, which one of FIGS. 7B to 7D the video scene matches is determined, and an evaluation condition corresponding to that video scene is obtained in S606. Specifically, a threshold value for the amount of apparent motion of the background in the video is obtained as the evaluation condition. In S607, the video evaluation unit 333 determines the amount of motion of the background on the basis of the virtual camera parameters and, if the amount of apparent motion of the background in the virtual viewpoint video corresponding to those virtual camera parameters is more than the threshold value obtained in S606, the video evaluation unit 333 determines that the evaluation target frame is a frame image that causes visually-induced motion sickness. The result of the determination contains the frame number of the frame image that exceeded the evaluation condition (i.e. the frame image determined to cause visually-induced motion sickness). The result of the determination also contains the foreground image area or background image area that exceeded the evaluation condition (i.e. the foreground image area or background image area determined to cause visually-induced motion sickness).

<Visually-Induced Motion Sickness Warning Display>

Figure 9:
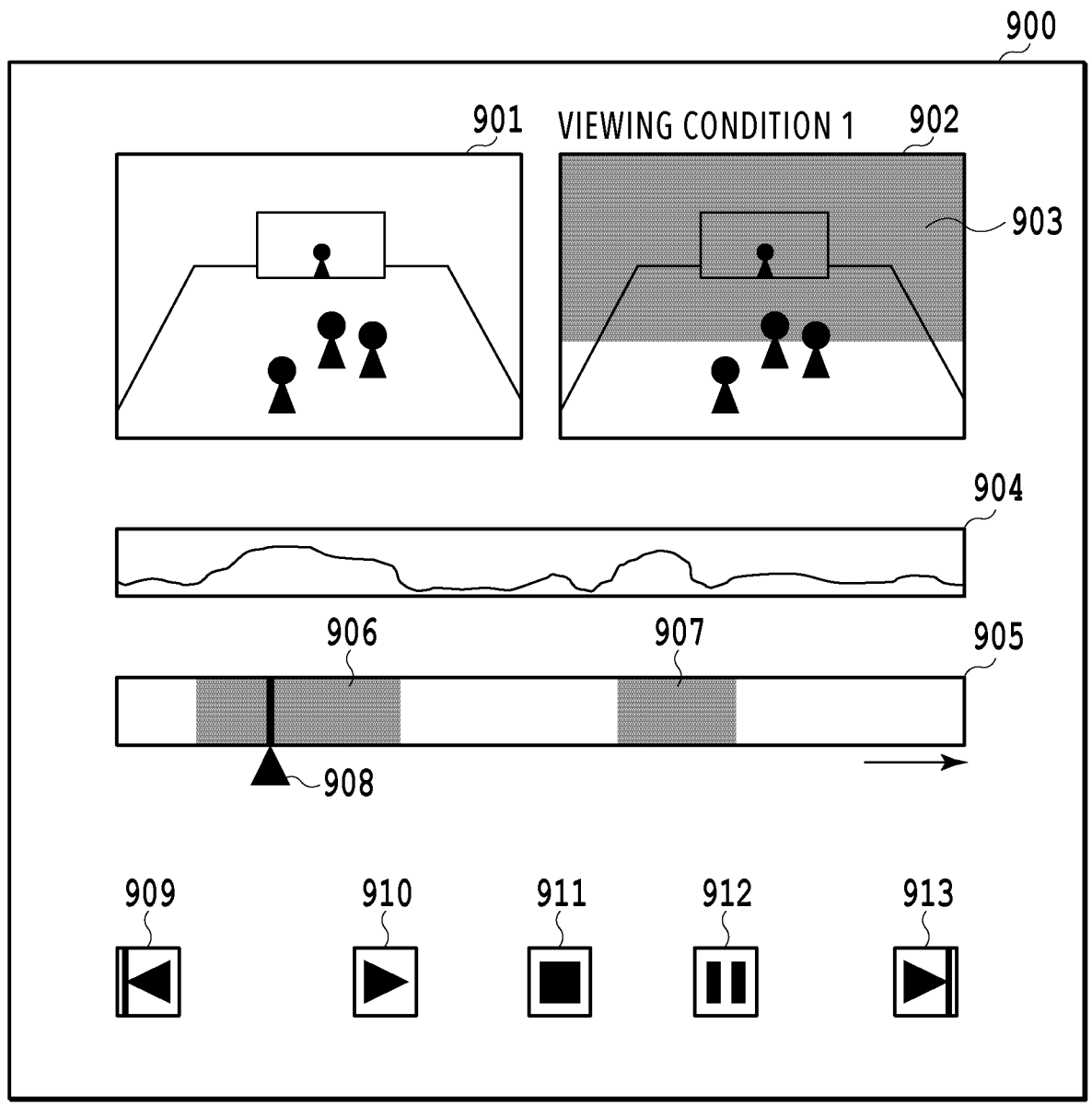
FIG. 9 is a diagram illustrating an example of a GUI screen provided by the image processing apparatus.

FIG. 9 illustrates an example of a UI screen 900 displaying the result of a visually-induced motion sickness evaluation on a virtual viewpoint video. The UI screen 900 is displayed on the display unit 104.

In the UI screen 900 for the result of a visually-induced motion sickness evaluation, a timeline 905 represents a frame range corresponding to the playback period of the virtual viewpoint image. A pointer 908 designates a frame image displayed in a frame image display area 901. Also, any frame for which a visually-induced motion sickness under the set viewing condition should be warned of is displayed in a recognizable manner on the timeline 905, like frame warning displays 906 and 907. A visually-induced motion sickness evaluation value display area 904 indicates a visually-induced motion sickness evaluation element calculated for each frame. In the visually-induced motion sickness evaluation value display area 904, for example, the value of apparent speed in the video, the amount of change in motion vector in the video, or the like is displayed. The likelihood of motion sickness in the visually-induced motion sickness evaluation result may be quantified and that quantified result may be displayed in the visually-induced motion sickness evaluation value display area 904.

A warning image display area 902 is synchronized with the frame image displayed in the frame image display area 901. In the warning image display area 902, an image area 903 that can be a cause of visually-induced motion sickness under the set viewing condition in the frame image displayed in the frame image display area 901 is highlighted. Video playback operation buttons 909 to 913 are buttons for performing playback operations such as starting and stopping playback of the virtual viewpoint video displayed in the frame image display area 901.

Note that the description has been given by taking as an example a case where a single viewing condition is set for the sake of description. However, a plurality of viewing conditions may be set, and a visually-induced motion sickness evaluation may be performed for each of them. Moreover, in the UI screen 900, sets of the warning image display area 902, the visually-induced motion sickness evaluation value display area 904, and the timeline 905 for the respective viewing conditions may be displayed side by side for the respective conditions. Alternatively, a button to switch between the viewing conditions may be provided, and the UI screen 900 may be switched in response to an operation on the button by the user.

In the example presented, the visually-induced motion sickness evaluation in this embodiment involves determining whether a video causes visually-induced motion sickness, on the basis of whether it exceeds a visually-induced motion sickness evaluation condition. However, it is possible to employ a configuration that outputs an evaluation value among graduated numerical values obtained by converting degrees of visually-induced motion sickness caused by types of video scene and amounts of motion of the foreground or background. For example, since visually-induced motion sickness occurs in a case where the amount of motion exceeds a threshold value, it is possible to output an evaluation value obtained by quantifying intervals up to the point at which the amount of motion exceeds the threshold value. In this example, the higher the evaluation value, the more likely visually-induced motion sickness occurs. In a case where the amount of motion further increases after exceeding the threshold value, motion sickness conversely tends not to occur. Thus, after the amount of motion exceeds the threshold value, the evaluation value may be caused to decrease the further the amount of motion increases. Also, the tendency of occurrence of visually-induced motion sickness varies by the type of motion (vertical motion, horizontal motion, rotational motion, etc.). Thus, an evaluation value corresponding to that tendency may be output.

As described above, in the process performed in this embodiment, the amounts of motion of the foreground image area and the background image area in an evaluation target frame in a virtual viewpoint video are obtained. Also, the virtual camera path in the evaluation target frame is obtained. Then, an evaluation condition corresponding to these pieces of information is determined. For example, the visually-induced motion sickness evaluation unit 330 determines the video scene of the evaluation target frame and determines an evaluation condition suitable for video scene. Then, the visually-induced motion sickness evaluation unit 330 evaluates visually-induced motion sickness due to the evaluation target frame by using the determined evaluation condition. By performing such a process, an accurate visually-induced motion sickness evaluation suitable for the video scene is performed. In virtual viewpoint videos, there can be video scenes that are similar in foreground and background motions but are totally different in virtual camera path. According to this embodiment, which one of the scenes of FIGS. 7B to 7D the video scene is, for example, is determined by using the foreground or background motion and the virtual camera path. Then, by using an evaluation condition suitable for that video scene, visually-induced motion sickness is evaluated accurately.

Embodiment 2

In embodiment 1, description has been given of an image processing apparatus that evaluates visually-induced motion sickness due to an input virtual viewpoint video and displays a warning for any frame range and image area in the virtual viewpoint video where the degree of visually-induced motion sickness exceeds a predetermined threshold value. In this embodiment, description will be given of a configuration enabling the user to easily correct a virtual camera parameter(s) to reduce visually-induced motion sickness.
<Configuration of Image Processing Apparatus>

Figure 10:
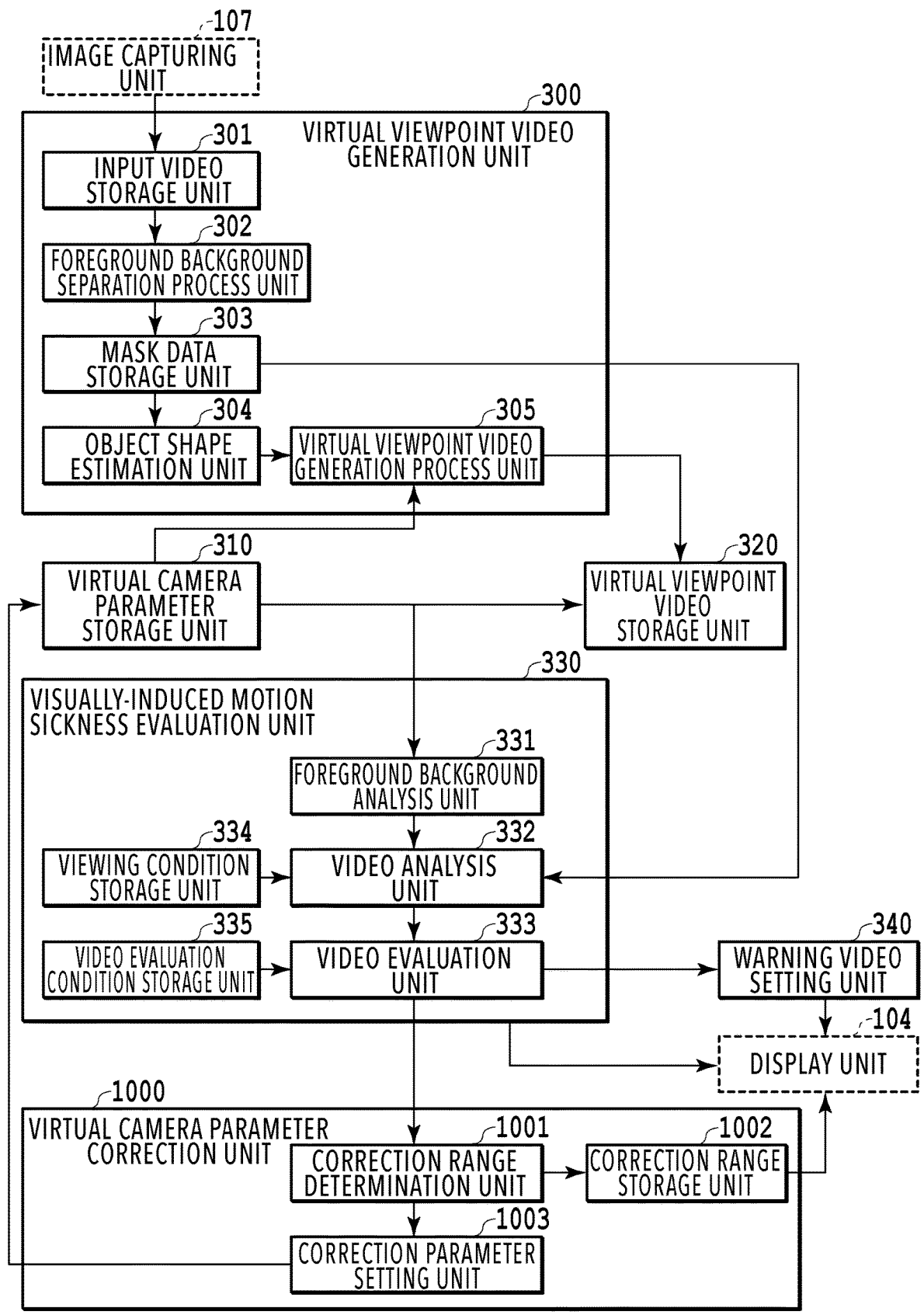
FIG. 10 is a diagram illustrating an example of the logical configuration of an image processing apparatus.

FIG. 10 is a diagram illustrating an example of the logical configuration of an image processing apparatus 100 in embodiment 2. It has the configuration described in embodiment 1 with a virtual camera parameter correction unit 1000 further included therein. The other features of the configuration are similar to those in embodiment 1. The virtual camera parameter correction unit 1000 determines a recommendable virtual camera parameter(s) (within a range that reduces visually-induced motion sickness) by using the result of the evaluation performed by the visually-induced motion sickness evaluation unit 330. For example, the virtual camera parameter correction unit 1000 changes a virtual camera parameter(s) in a stepwise manner. The visually-induced motion sickness evaluation unit 330 evaluates visually-induced motion sickness due to a virtual viewpoint video generated using the changed virtual camera parameter. By using the result of that evaluation, the virtual camera parameter correction unit 1000 determines a virtual camera parameter within a range in which visually-induced motion sickness does not occur. The user can set the virtual camera parameter within that determined range. The virtual camera parameter correction unit 1000 corrects the virtual camera parameter by replacing (changing) the virtual camera parameter stored in the virtual camera parameter storage unit 310 with the set virtual camera parameter. Then, a virtual viewpoint video using the corrected virtual camera parameter is generated. Meanwhile, instead of replacing the stored virtual camera parameter, another virtual camera parameter representing a virtual viewpoint determined on the basis of a user operation may be additionally stored. The configuration of the virtual camera parameter correction unit 1000 will be described below.

The virtual camera parameter correction unit 1000 includes a correction range determination unit 1001, a correction range storage unit 1002, and a correction parameter setting unit 1003. On the basis of the virtual camera parameter used for a virtual viewpoint video determined to cause visually-induced motion sickness, the correction range determination unit 1001 determines a possible virtual camera parameter correction range in which visually-induced motion sickness does not occur. The determined possible correction range is stored in the correction range storage unit 1002. The possible virtual camera parameter correction range is presented to the user through the display unit 104. The correction parameter setting unit 1003 sets a corrected value of the virtual camera parameter designated within the possible correction range by the user. Specifically, the correction parameter setting unit 1003 stores that corrected value (corrected virtual camera parameter) in the virtual camera parameter storage unit 310. The virtual viewpoint video generation unit 300 generates a virtual viewpoint video with reduced visually-induced motion sickness by using the corrected virtual camera parameter. In this embodiment, the correction of the virtual camera parameter will be described by taking as an example a process of correcting the coordinates of the virtual camera.

Figure 11:
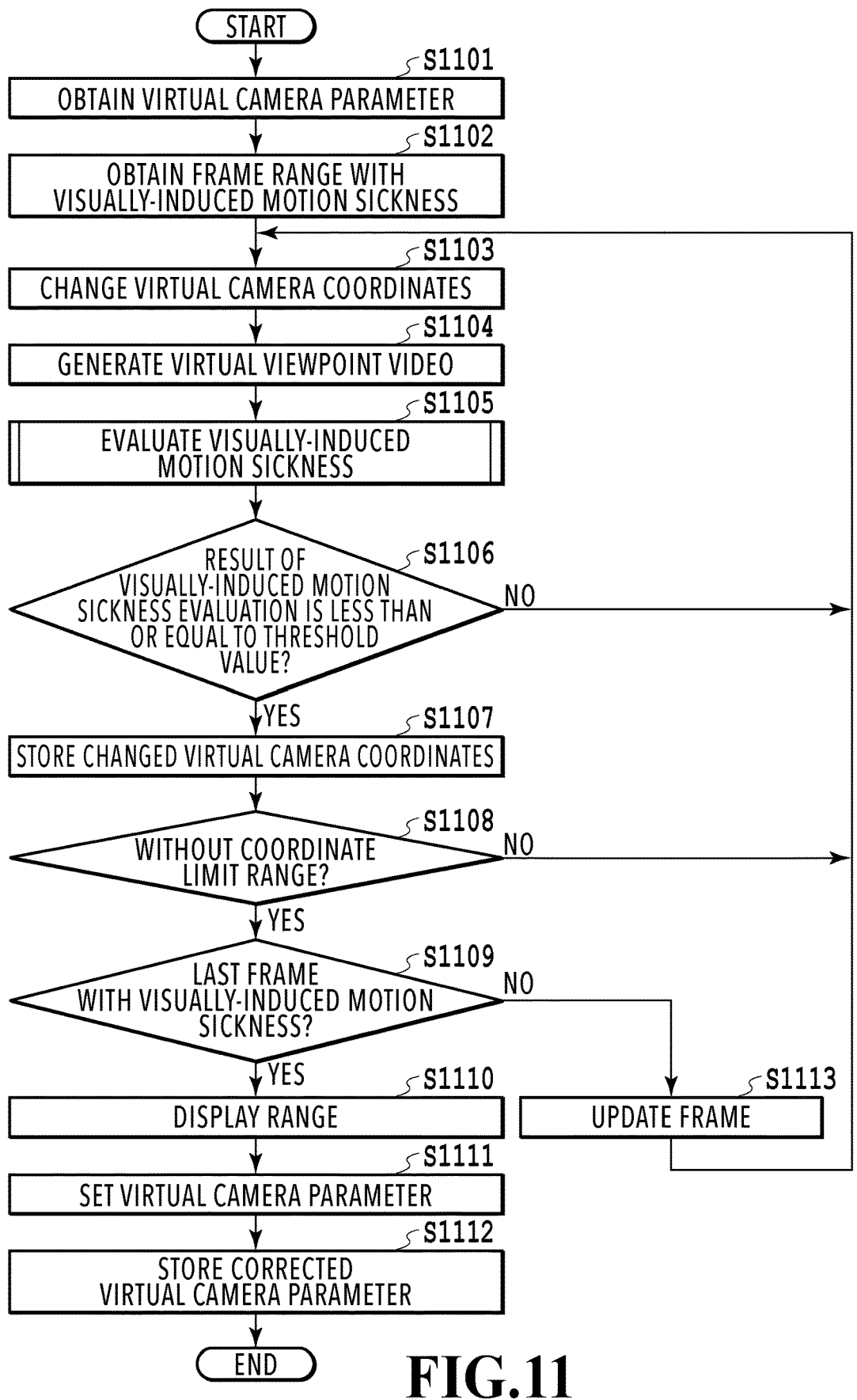
FIG. 11 is a flowchart describing the flow of a process by the image process apparatus.

FIG. 11 is a flowchart describing a series of processes performed in the image processing apparatus 100 after performing a visually-induced motion sickness evaluation on a virtual viewpoint video to correct the virtual camera parameter in a frame range determined to cause visually-induced motion sickness.

In S1101, the virtual camera parameter correction unit 1000 obtains the virtual camera parameter used for the virtual viewpoint video. The virtual camera parameter includes the camera coordinate values, the camera orientation, the focal length, and so on in each of the video frames (frame images) along the time axis inside the virtual space for generating the virtual viewpoint video.

Figure 12A:
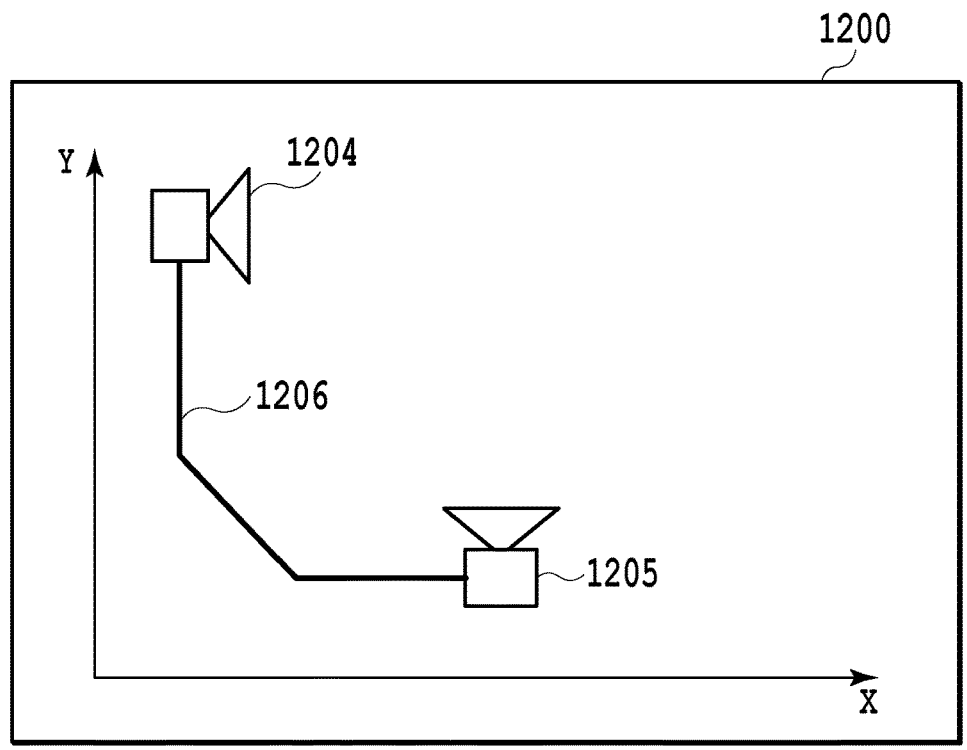
FIGS. 12A and 12B are diagrams illustrating an example of UI screens indicating virtual camera coordinates.
Figure 12B:
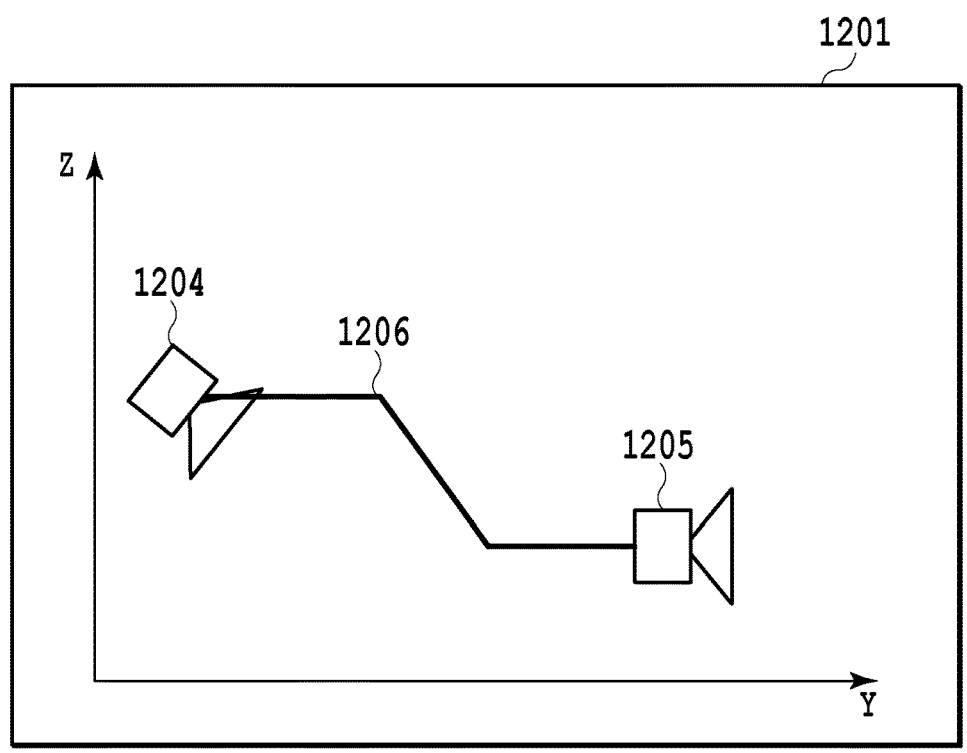

FIGS. 12A and 12B are an example of a UI illustrating the coordinates of the virtual camera included in the obtained virtual camera parameter (hereinafter, referred to as the virtual camera coordinates). In this embodiment, a three-dimensional virtual space is used to generate the virtual viewpoint video. On a UI screen 1200, plane coordinates in the virtual space are displayed as a XY plane. On a UI screen 1201, a YZ plane in the virtual space is displayed with the height in the virtual space being the Z axis. The virtual camera path in the virtual viewpoint video is illustrated by a start point 1204, an end point 1205, and a track 1206 representing the change in virtual camera coordinates between them.

In S1102, the virtual camera parameter correction unit 1000 obtains the frame range evaluated to cause visually-induced motion sickness from the result of the visually-induced motion sickness evaluation on the virtual viewpoint video data.

In S1103, the correction range determination unit 1001 changes the virtual camera coordinates in the first frame image to be processed in the frame range evaluated to cause visually-induced motion sickness, by a given coordinate data interval. Note that in this embodiment, a limit has been set in advance on the range within which to change the virtual camera coordinates, and the given coordinate data interval is set to a value within the limit. In this embodiment, as also described later, the virtual camera coordinates are changed from the first coordinates obtained in S1101 to second coordinates, which are different coordinates, and visually-induced motion sickness due to a virtual viewpoint video generated using the changed second coordinates is evaluated. Then, if the virtual viewpoint video does not cause visually-induced motion sickness, the second coordinates are determined as a correction range. Thereafter, the virtual camera coordinates are changed to third coordinates, which are different from the second coordinates, and similar processes are repeated. As a result, the correction range for the first frame image is determined. These processes are performed for all frame images in the frame range.

Figure 13A:
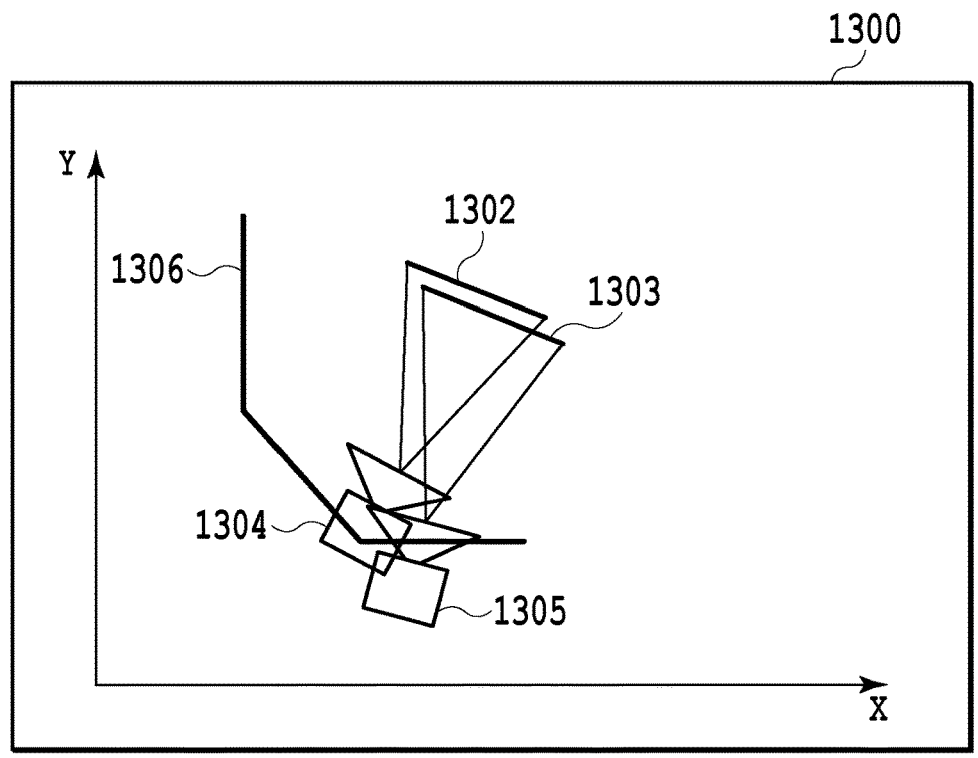
FIGS. 13A and 13B are diagrams illustrating an example of setting a limit on the area within which to change the virtual camera coordinates.
Figure 13B:
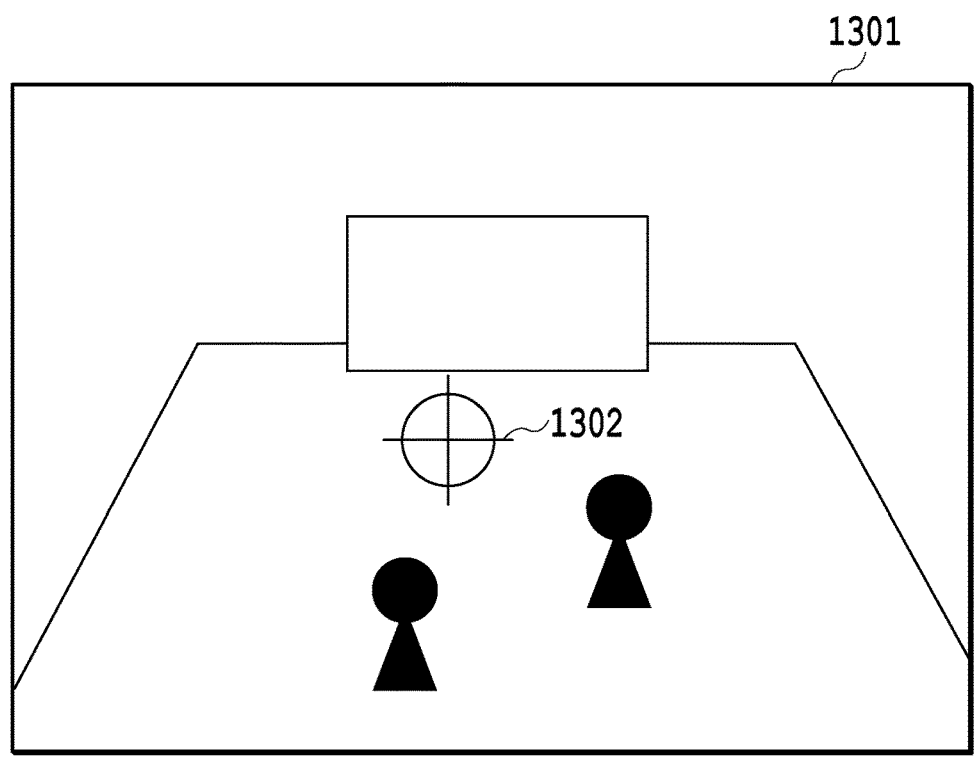

FIGS. 13A and 13B are diagrams explaining an example of setting a limit on the range within which to change the virtual camera coordinates. FIG. 13A illustrates an XY plane coordinate system 1300 in the virtual space of the virtual viewpoint video. In the XY plane coordinate system 1300, virtual camera coordinates 1304 on an input virtual camera path 1306 are displayed. FIG. 13B is a frame image 1301 in the virtual viewpoint video corresponding to the virtual camera coordinates 1304. A virtual camera viewpoint area 1302 in the frame image 1301 represents the same area as a virtual camera viewpoint area 1302 in the XY plane coordinate system 1300. The virtual camera viewpoint area 1302 is an area covering a predetermined range including the gazing point. Assume that the virtual camera coordinates 1304 are to be changed to different coordinates to correct the virtual camera parameter. In this case, a predetermined limit is set on the amount of movement from the virtual camera viewpoint area 1302 to a virtual camera viewpoint area 1303, which is the destination. In other words, the virtual camera viewpoint area 1303, which is the destination, is set within the range defined by the predetermined limit. In this way, a limit can be set on the change of the virtual camera coordinates within such a range the frame image 1301 from the virtual camera viewpoint does not change greatly.

In S1104, the correction range determination unit 1001 generates a virtual viewpoint video using the corrected virtual camera coordinates. The correction range determination unit 1001 can generate the virtual viewpoint video by a process similar to the process performed in the virtual viewpoint video generation unit 300. Alternatively, the correction range determination unit 1001 may cause the virtual viewpoint video generation unit 300 to generate the virtual viewpoint video.

In S1105, the correction range determination unit 1001 performs a visually-induced motion sickness evaluation on the virtual viewpoint video generated using the changed virtual camera coordinates. The correction range determination unit 1001 can perform the visually-induced motion sickness evaluation by a process similar to the process performed in the visually-induced motion sickness evaluation unit 330. Alternatively, the correction range determination unit 1001 may cause the visually-induced motion sickness evaluation unit 330 to perform the visually-induced motion sickness evaluation.

In S1106, the correction range determination unit 1001 determines whether the result of the visually-induced motion sickness evaluation in S1105 exceeds a predetermined threshold value. If the result of the evaluation exceeds the predetermined threshold value, the correction range determination unit 1001 returns to the process in S1103, in which it further changes the virtual camera coordinates by the given interval, and repeats the processes in S1104 and S1105.

If the result of the evaluation does not exceed the predetermined threshold value, then in S1107, the correction range determination unit 1001 stores the virtual camera coordinates changed in S1103 in the correction range storage unit 1002 as virtual camera coordinates that do not cause visually-induced motion sickness.

In S1108, the correction range determination unit 1001 determines the virtual camera coordinates changed in S1103 are within the predetermined limit, and repeats the processes in and after S1103 are repeated if the virtual camera coordinates are within the limit. If the virtual camera coordinates are outside the limit, then in S1109, the correction range determination unit 1001 determines whether the processes in S1103 to S1108 have been executed on all frames in the frame range evaluated to cause visually-induced motion sickness.

If the processes have not been completed for all frames, the correction range determination unit 1001 updates the target frame in S1113 and repeats the processes in and after S1103. If the processes have been completed for all frames, then in S1110, the virtual camera parameter correction unit 1000 displays the possible virtual camera coordinate correction range stored in the correction range storage unit 1002 to the user.

In S1111, the correction parameter setting unit 1003 sets a virtual camera parameter in the frame range evaluated to cause visually-induced motion sickness, within the possible correction range on the basis of a designation from the user. Note that although the virtual camera parameter in the frame range evaluated to cause visually-induced motion sickness is determined on the basis of a designation from the user, this may be omitted. Specifically, the image processing apparatus 100 may change the virtual camera parameter in the frame range evaluated to cause visually-induced motion sickness to a virtual camera parameter that can be evaluated not to cause visually-induced motion sickness automatically without receiving a designation from the user. As a result, the virtual camera parameter is corrected. In S1112, the correction parameter setting unit 1003 stores the corrected virtual camera parameter in the virtual camera parameter storage unit 310. By the above step, the process in this flowchart ends.

Figure 14A:
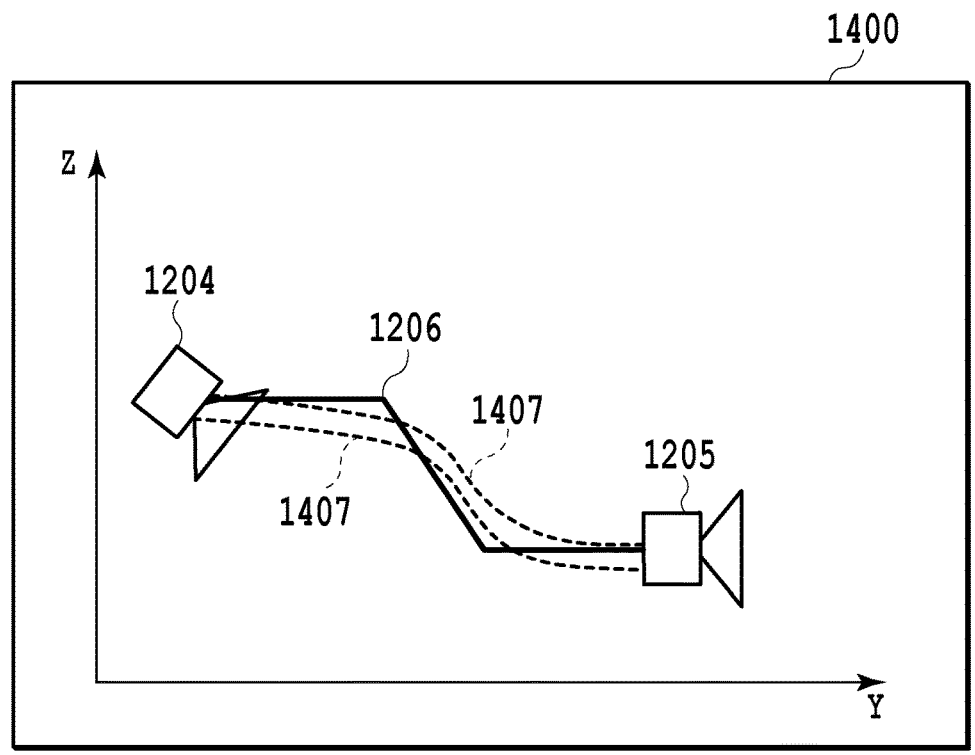
FIGS. 14A and 14B are diagrams illustrating examples of UI screens indicating possible correction ranges.
Figure 14B:
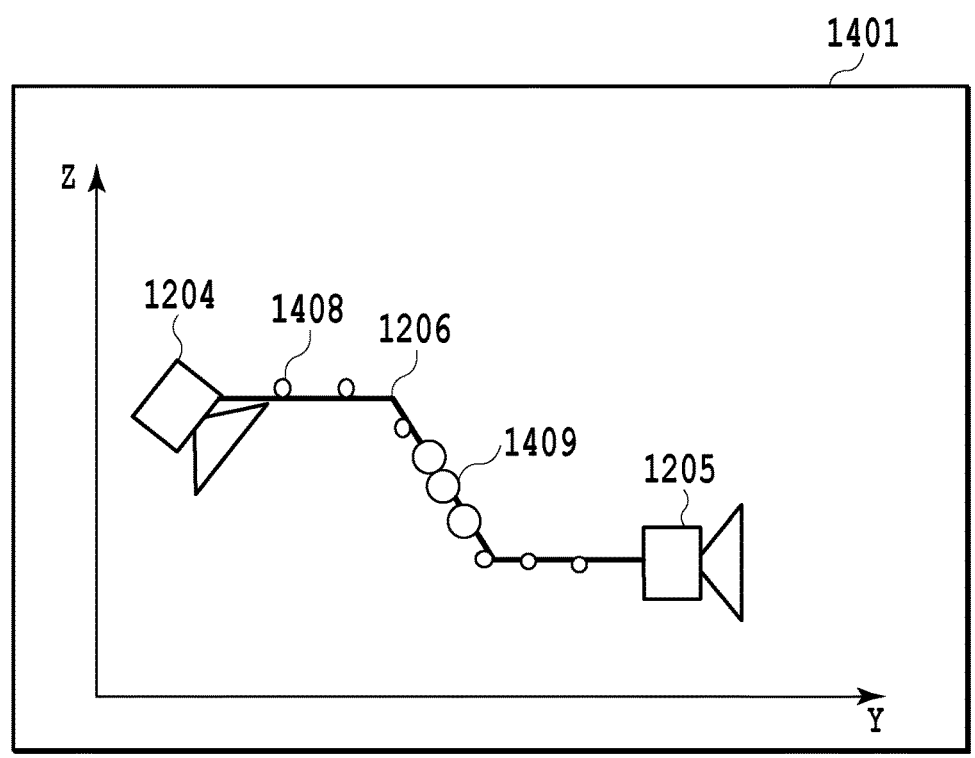

FIGS. 14A and 14B are diagrams illustrating examples of UI screens each displaying a possible correction range. A UI screen 1400 illustrated in FIG. 14A is a UI screen displaying a possible correction range for the virtual camera coordinates illustrated in FIG. 12A. On the UI screen 1400, the range defined between the dotted lines is displayed as a possible correction range 1407 for the track 1206 of the virtual camera coordinates on a YZ plane in the virtual space.

The user can correct the virtual camera coordinates by changing the track 1206 on the UI screen 1400 such that the track 1206 is located within the possible correction range 1407. The corrected virtual camera coordinates are stored in the virtual camera parameter storage unit 310.

Note that in this embodiment, description has been given of the process in which the virtual camera position is changed for virtual camera parameter correction. However, a similar process can be used as a virtual camera parameter correction process for correcting a different virtual camera parameter.

FIG. 14B illustrates a UI screen 1401 for correcting the playback speed of a virtual viewpoint video as an example of the correction of a different virtual camera parameter. The UI screen 1401, illustrated in FIG. 14B, illustrates the virtual camera coordinates illustrated in FIG. 12B. The UI screen 1401 illustrates a possible correction range for the playback speed. On the UI screen 1401, each white circle 1408 on the track 1206 of the virtual camera coordinates in the virtual viewpoint video indicates the camera coordinates in a frame. The maximum playback speed of the virtual viewpoint video is the frame rate of the input video data. Here, during playback, the same frame is assigned successively to a predetermined frame(s) in the virtual viewpoint video. In this way, the playback speed can be lowered. Thus, by setting the number of same frames to be reproduced at desired virtual camera coordinates in a virtual viewpoint video, it is possible to control the playback speed of the virtual viewpoint video while changing the virtual camera coordinates. On the UI screen 1401, the number of same frames at the camera coordinates in each frame is indicated by the size of a white circle 1409. Thus, on the UI screen 1401, a possible playback speed correction range in which visually-induced motion sickness does not occur (upper limit frame rate) is displayed by varying the size of the white circle 1409 on the basis of the result of the visually-induced motion sickness evaluation.

Note that in the processes in S1106 to S1110 in the flowchart of FIG. 11, a plurality of threshold values can be set for a visually-induced motion sickness evaluation result, and possible correction ranges corresponding to the plurality of threshold values may be calculated. Then, the possible correction ranges corresponding to the plurality of threshold values can be displayed on the UI screens 1400 and 1401.

Note that the virtual camera parameter correction unit 1000 may be configured to obtain profile information on user characteristics and perform a correction process suitable for the user's profile in a case where the user corrects any virtual camera parameter. For example, in a case where the user is a professional in video production and editing, the number of virtual camera parameters to be corrected and the possible correction ranges may be set to wide ranges covering ranges in which mild visually-induced motion sickness occurs, for example. In this way, the degree of freedom in correction can be enhanced. In short, in the limiting of a possible correction range, that limit may be set to be looser than a first limit (the possible correction range may be widened).

On the other hand, for a normal user without a video production expertise or knowledge on visually-induced motion sickness, the number of virtual camera parameters to be corrected and the possible correction ranges may be limited to ranges in which the likelihood of occurrence of visually-induced motion sickness is low. In this way, a virtual viewpoint video with reduced visually-induced motion sickness can be generated. In short, in the limiting of a possible correction range, that limit may be set to be stricter than the first limit (the possible correction range may be narrowed).

As described above, according to this embodiment, by using the result of a visually-induced motion sickness evaluation on a virtual viewpoint video, it is possible to present to the user a possible correction range representing a range in which visually-induced motion sickness does not occur. Then, the user can correct the virtual camera parameter within the presented possible correction range. With such a process, the user can correct the virtual camera parameter within a range in which visually-induced motion sickness does not occur. Thus, the user can avoid an operation of re-setting the virtual camera parameter of the virtual viewpoint video.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

According to the present disclosure, visually-induced motion sickness due to a virtual viewpoint video can be accurately evaluated.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-036651, filed Mar. 1, 2018, which is hereby incorporated by reference wherein in its entirety.

What is claimed is:

1. An information processing apparatus comprising:
   a first obtaining unit configured to obtain viewpoint information indicating change of a virtual viewpoint corresponding to a virtual viewpoint video generated on a basis of a plurality of images captured from a plurality of directions with a plurality of image capturing apparatuses;
   a second obtaining unit configured to obtain condition information indicating a condition associated with an amount of change of a background in the virtual viewpoint video;
   a determination unit configured to determine whether the viewpoint information obtained by the first obtaining unit satisfies the condition indicated by the condition information obtained by the second obtaining unit; and
   an output unit configured to output information according to a result of the determination by the determination unit.

2. The information processing apparatus according to claim 1, wherein the information output from the output unit is information indicating an evaluation on visually-induced motion sickness due to the virtual viewpoint video.

3. The information processing apparatus according to claim 2, wherein
   on a basis of the viewpoint information obtained by the first obtaining unit, the determination unit determines whether the amount of change of the background in the virtual viewpoint video corresponding to the viewpoint information exceeds a threshold value corresponding to the condition information obtained by the second obtaining unit, and
   the output unit outputs information indicating that the virtual viewpoint video causes visually-induced motion sickness, in a case where the determination unit determines that the amount of change of the background exceeds the threshold value.

4. The information processing apparatus according to claim 1, wherein the condition information obtained by the second obtaining unit further indicates a condition associated with an amount of change of a foreground in the virtual viewpoint video.

5. The information processing apparatus according to claim 1, wherein the condition information obtained by the second obtaining unit indicates a condition corresponding to an environment in which the virtual viewpoint video is to be viewed by a user.

6. The information processing apparatus according to claim 1, wherein the condition information obtained by the second obtaining unit indicates a condition corresponding to a pattern of movement of the virtual viewpoint.

7. The information processing apparatus according to claim 1, further comprising a display control unit configured to cause a display unit to display an image corresponding to the information output from the output unit.

8. The information processing apparatus according to claim 7, wherein the display control unit causes the display unit to display information representing a virtual viewpoint recommended on a basis of the information output from the output unit.

9. The information processing apparatus according to claim 1, wherein the output unit outputs information indicating the result of the determination by the determination unit and information for identifying a frame in the virtual viewpoint video according to the result of the determination, as the information according to the result of the determination.

10. The information processing apparatus according to claim 1, wherein the output unit outputs information indicating the result of the determination by the determination unit and information indicating an area in the virtual viewpoint video in which the amount of change of the background is more than or equal to a threshold value, as the information according to the result of the determination.

11. The information processing apparatus according to claim 1, wherein
the determination unit determines whether the viewpoint information satisfies the condition indicated by the condition information, for each of a plurality of periods in a playback period of the virtual viewpoint video, and
the output unit outputs information according to a result of the determination on each of the plurality of periods in the playback period.

12. The information processing apparatus according to claim 1, further comprising a changing unit configured to change the viewpoint information obtained by the first obtaining unit, on a basis of the information output from the output unit.

13. The information processing apparatus according to claim 1, further comprising a determination unit configured to determine a playback speed of the virtual viewpoint video on a basis of the information output from the output unit.

14. The information processing apparatus according to claim 1, further comprising:
a third obtaining unit configured to obtain other viewpoint information indicating a virtual viewpoint determined on a basis of a user operation, after the output unit outputs the information according to the result of the determination; and
a generation unit configured to generate a virtual viewpoint video on a basis of the other viewpoint information determined by the third obtaining unit.

15. The information processing apparatus according to claim 14, wherein the third obtaining unit determines the other virtual viewpoint on a basis of an input according to the user operation and user information.

16. The information processing apparatus according to claim 1, wherein
the background is an area in the virtual viewpoint video other than a foreground corresponding to a predetermined object, and
the background in the virtual viewpoint video changes in accordance with change of the virtual viewpoint corresponding to the virtual viewpoint video.

17. The information processing apparatus according to claim 1, wherein the viewpoint information obtained by the first obtaining unit indicates a position and direction of the virtual viewpoint at each of a plurality of time points.

18. The information processing apparatus according to claim 1, wherein the determination unit determines whether the viewpoint information satisfies the condition indicated by the condition information, on a basis of a position and direction of the virtual viewpoint indicated by the viewpoint information in a three-dimensional space and a position of an object in the three-dimensional space.

19. An information processing method comprising:
obtaining viewpoint information indicating change of a virtual viewpoint corresponding to a virtual viewpoint video generated on a basis of a plurality of images captured from a plurality of directions with a plurality of image capturing apparatuses;
obtaining condition information indicating a condition associated with an amount of change of a background in the virtual viewpoint video;
determining whether the obtained viewpoint information satisfies the condition indicated by the condition information; and
outputting information according to a result of the determination.

20. A non-transitory computer readable storage medium storing a program which performs an image processing method, the method comprising:
obtaining viewpoint information indicating change of a virtual viewpoint corresponding to a virtual viewpoint video generated on a basis of a plurality of images captured from a plurality of directions with a plurality of image capturing apparatuses;
obtaining condition information indicating a condition associated with an amount of change of a background in the virtual viewpoint video;
determining whether the obtained viewpoint information satisfies the condition indicated by the condition information; and
outputting information according to a result of the determination.

* * * * *